United States Patent
Leopoldo et al.

(10) Patent No.: US 7,488,730 B2
(45) Date of Patent: Feb. 10, 2009

(54) N-(1,2,3,4-TETRAHYDRONAPHTHALEN-1-YL)-4-PHENYL-1-PIPERAZINEALKYLAMIDE DERIVATIVES, AND THERAPEUTIC USE THEREOF AS 5-HT₇ RECEPTOR LIGANDS

(75) Inventors: Marcello Leopoldo, Bari (IT); Francesco Berardi, Bari (IT); Nicola Antonio Colabufo, Triggiano (IT); Marialessandra Contino, Taranto (IT); Enza Lacivita, Pallazo S. Gervasio (IT); Mauro Niso, Martina Franca (IT); Roberto Perrone, Bari (IT); Vincenzo Tortorella, Bari (IT)

(73) Assignee: Universita Degli Studi Di Bari, Bari (IT)

( * ) Notice: Subject to any disclaimer, the term of this patent is extended or adjusted under 35 U.S.C. 154(b) by 122 days.

(21) Appl. No.: 11/283,608

(22) Filed: Nov. 18, 2005

(65) Prior Publication Data

US 2007/0117811 A1    May 24, 2007

(51) Int. Cl.
*A61K 31/495*    (2006.01)
*C07D 295/15*    (2006.01)
(52) U.S. Cl. .................. 514/255.03; 544/393
(58) Field of Classification Search ........................ None
See application file for complete search history.

(56) References Cited

OTHER PUBLICATIONS

Leopoldo et al. J. Med. Chem. vol. 47, p.6616-6624 (Nov. 19, 2004).*
Perrone et al. J.Med. Chem. vol.42, p.490-496 (1999).*
Roth et al. "The Role of Serotonin in Schizophrenia". Available at http://www.acnp.org/g4/GN401000117/CH115.html, 2000.*
Terron, European Journal of Pharmacology,vol.439, p.1-11 (2002).*

* cited by examiner

*Primary Examiner*—Emily Bernhardt
(74) *Attorney, Agent, or Firm*—Timothy H. Van Dyke; Beusse Wolter Sanks Mora & Maire

(57) ABSTRACT

A series of N-(1,2,3,4-tetrahydronaphthalen-1-yl)-4-aryl-1-piperazinealkylamides was prepared and their affinity for serotonin 5-HT₇, 5-HT$_{1A}$, and 5-HT$_{2A}$ receptors was measured using in vitro binding assays. In relation to 5-HT₇ receptor affinity, receptor binding studies indicated that: (i) the optimal alkyl chain length was five methylenes; (ii) an unsubstituted 1,2,3,4-tetrahydronaphthalenyl nucleus was selected for further substitutions; and (iii) the substitution pattern of the aryl ring linked to the piperazine ring played a significant role. Several compound with high affinity for 5-HT₇ receptors were identified. Among them, 4-(2-methoxyphenyl)-N-(1,2,3,4-tetrahydronaphthalen-1-yl)-1-piperazinehexanamide (28), 4-(2-acetylphenyl)-N-(1,2,3,4-tetrahydronaphthalen-1-yl)-1-piperazinehexanamide (34), 4-(2-methylthiophenyl)-N-(1,2,3,4-tetrahydronaphthalen-1-yl)-1-piperazinehexanamide (44), 4-(2-hydroxyphenyl)-N-(1,2,3,4-tetrahydronaphthalen-1-yl)-1-piperazinehexanamide (46), 4-(2-methylphenyl)-N-(1,2,3,4-tetrahydronaphthalen-1-yl)-1-piperazinehexanamide (49) were assayed for the 5-HT₇ receptor mediated relaxation of substance P-induced guinea-pig ileum contraction. Compounds 28, 44, and 49 behaved as full agonists, compound 34 as a partial agonist, whereas derivative 46 acted as an antagonist.

12 Claims, 3 Drawing Sheets

Reagents: (A) ω-haloacyl chloride, NaOH; (B) 1-arylpiperazine; (C) ethyl 3-chloropropanoate; (D) NaOH; (E) 9d, carbonyl diimidazole.

FIGURE 3

N-(1,2,3,4-TETRAHYDRONAPHTHALEN-1-YL)-4-PHENYL-1-PIPERAZINEALKYLAMIDE DERIVATIVES, AND THERAPEUTIC USE THEREOF AS 5-HT$_7$ RECEPTOR LIGANDS

FIELD OF THE INVENTION

The present invention relates to a novel family of 5-HT$_7$ Receptor ligands, being derivatives of N-(1,2,3,4-tetrahydronaphthalen-1-yl)-4-(2-substituted-phenyl)-1-piperazinealkylamide, and to their therapeutic use in the treatment of all those states suitable to be relieved by 5-HT$_7$ receptor agonists or antagonists.

BACKGROUND OF THE INVENTION

The neurotransmitter serotonin (5-hydroxytryptamine, 5-HT) has an array of pharmacological and physiological roles within the central nervous system (CNS) and in the periphery, mediated by its interactions with a total of 14 structurally and pharmacologically distinct receptor subtypes. These receptors have been assigned to one of seven families, 5-HT$_{1-7}$. The 5-HT$_7$ receptor (5-HT$_7$R) is the most recent addition to the 5-HT receptor family, and was cloned for the first time in 1993 from rat and mouse. Since then, it has been cloned from other species such as human, guinea-pig, and pig. The 5-HT$_7$R was shown to be positively coupled to adenylyl cyclase via Gs proteins. It displays a low degree of homology (40%) with other Gs-coupled 5-HT receptors. Four different isoforms have been found, namely 5-HT$_{7a}$, 5-HT$_{7b}$, 5-HT$_{7c}$, 5-HT$_{7d}$. Only two isoforms (5-HT$_{7a}$ and 5-HT$_{7b}$) are present in both rat and human, whereas the 5-HT$_{7c}$ receptor is found exclusively in rat, while the 5-HT$_{7d}$ is found only in human. Each of the isoforms appears to form a functionally active receptor with the 5-HT$_{7a}$, being the most abundant (80%) in both rat and human brain. There appear to be no pharmacological differences among the four isoforms. High concentrations of the 5-HT$_7$R have been detected by in situ hybridization and 5-HT$_7$-like immunoreactivity in the hypothalamus, entorhinal cortex, septal areas, substantia nigra, amygdala, rapes nuclei and the trigeminal nucleus. In addition, moderate levels of 5-HT$_7$-like immunoreactivity were found in the thalamus, hippocampus, cingulate and occipital cortex, caudate, putamen, and suprachiasmatic nucleus (SCN) of the rat. This distribution correlates well with distribution of mRNA encoding 5-HT$_7$R protein. In fact, the 5-HT$_7$R mRNA has been detected in thalamus, hypothalamus, hippocampus, amygdala, cortex, septum, and suprachiasmatic nucleus.

The potential of therapeutic effects of 5-HT$_7$ agents have been hypothesized on the basis of such anatomical distribution. The link between 5-HT$_7$Rs and the SCN suggests a potential role in circadian rhythms and sleep disorders. Lovenberg et al. (Lovenberg, T. W., Baron, B. M., de Lecea, L., Miller, J. D., Prosser, R. A., Rea, M. A., Foye, P. E., Racke, M., Slone, A. L., Siegel, B. W., Danielson, P. E., Sutcliffe, J. G., Erlander, M. G. *Neuron* 1993, 11, 449-458) demonstrated that phase advances in circadian neuronal activity of the SCN could be elicited using serotonergic ligands that display a pharmacological profile consistent with that of the 5-HT$_7$R. Since then, 5-HT$_7$Rs have been shown to be present in postsynaptic areas in the SCN where serotonergic neurones are proposed to play a key role in modulating circadian activity. Mullins et al.( Mullins, U. L.; Gianutsos, G.; Eison, A. S. *Neuropsychopharmacol.* 1999, 21, 352-367.) have supplied supporting evidence that implicates a possible role for 5-HT$_7$R in depression. They demonstrated that antidepressant-induced expression of the immediate early gene, c-Fos, in the SCN was blocked by ritanserin (a high-affinity, but non-selective, 5-HT$_7$R antagonist), but not by the 5-HT$_{1A}$ antagonist pindolol or the 5-HT$_{1D}$ antagonist sumatriptan. This suggests that the effect is mediated through 5-HT$_7$Rs, although, with such non-selective antagonists, the involvement of other 5-HT receptors cannot be ruled out.

The involvement of the 5-HT$_7$R in migraine pathogenesis has been proposed by Terron (Terron, J. A. *Eur. J. Pharmacol.* 2002, 439, 1-11) because the 5-HT$_7$R-mediated vasodilator mechanism operates in vascular structures that have been implicated in migraine, such as the middle cerebral and external carotid arteries. Finally, several compounds possessing high 5-HT$_7$R affinity have therapeutic indications as antipsychotic drugs and this has suggested that 5-HT$_7$R may mediate therapeutic action of such compounds (Roth, B. L.; Craigo, S. C.; Choudhary, M. S.; Uluer, A.; Monsma, F. J. Jr.; Shen, Y.; Meltzer, H. Y.; Sibley, D. R. *J. Pharmacol. Exp. Ther.* 1994, 268, 1403-1410).

Figure 1:
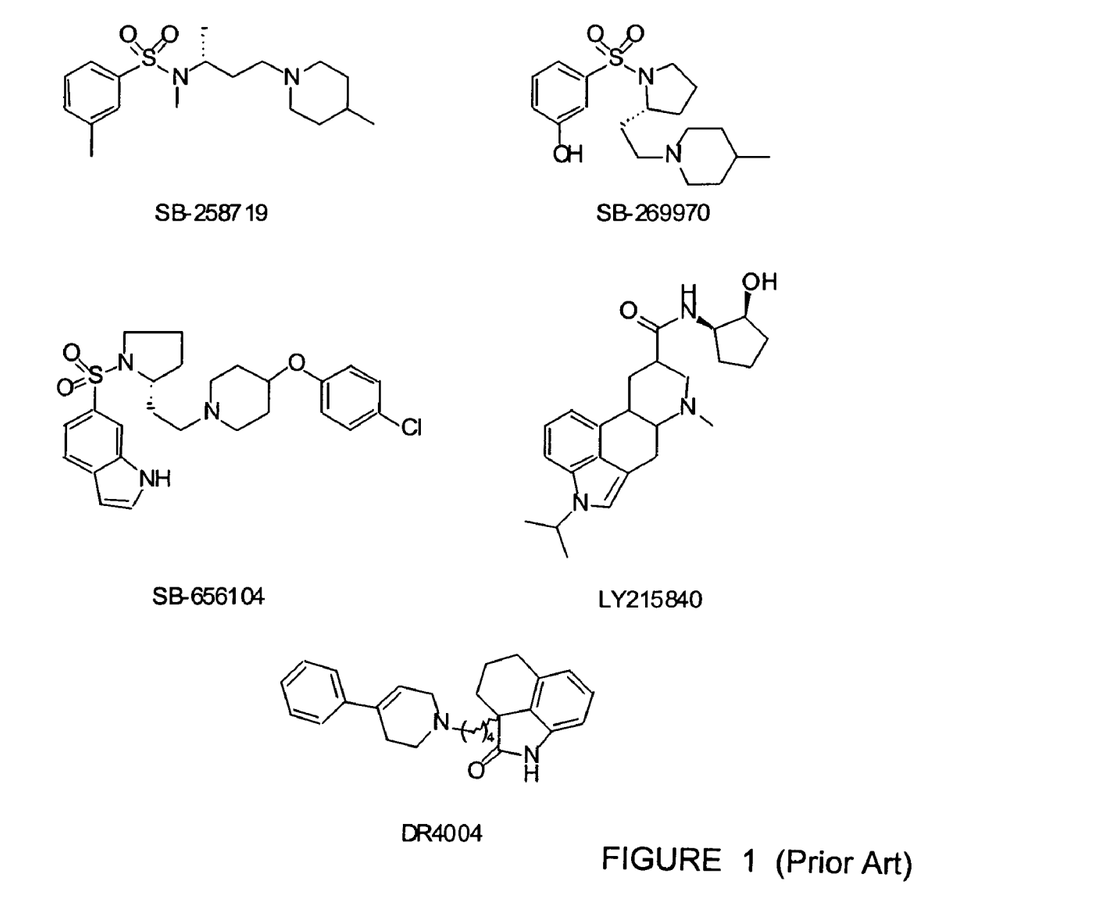
FIG. 1 provides the chemical structures of some prior art compounds developed as selective 5-HT$_7$R antagonists.

It is therefore clear that the 5-HT$_7$R may be a valuable drug target. During the last decade considerable research efforts have been directed towards the identification of selective 5-HT$_7$R antagonists, (Leopoldo, M. *Curr. Med. Chem.* 2004, 11, 629-661) allowing the identification of some interesting compounds such as SB-258719, SB-269970, SB-656104, DR4004, LY215840, the chemical structures of which are depicted in FIG. 1.

However, these promising compounds present several limitations because of their low potency (SB-258719), modest selectivity (SB-656104, LY215840), and low metabolic stability (SB-269970, DR4004).

Therefore, the scope of the present invention is that of providing novel selectively-acting 5-HT$_7$R ligands as useful pharmacological tools or potential drugs.

It is noteworthy that most 5-HT$_7$R ligands reported to date act as antagonists, whereas a very limited number of agonists has been reported.

Figure 2:
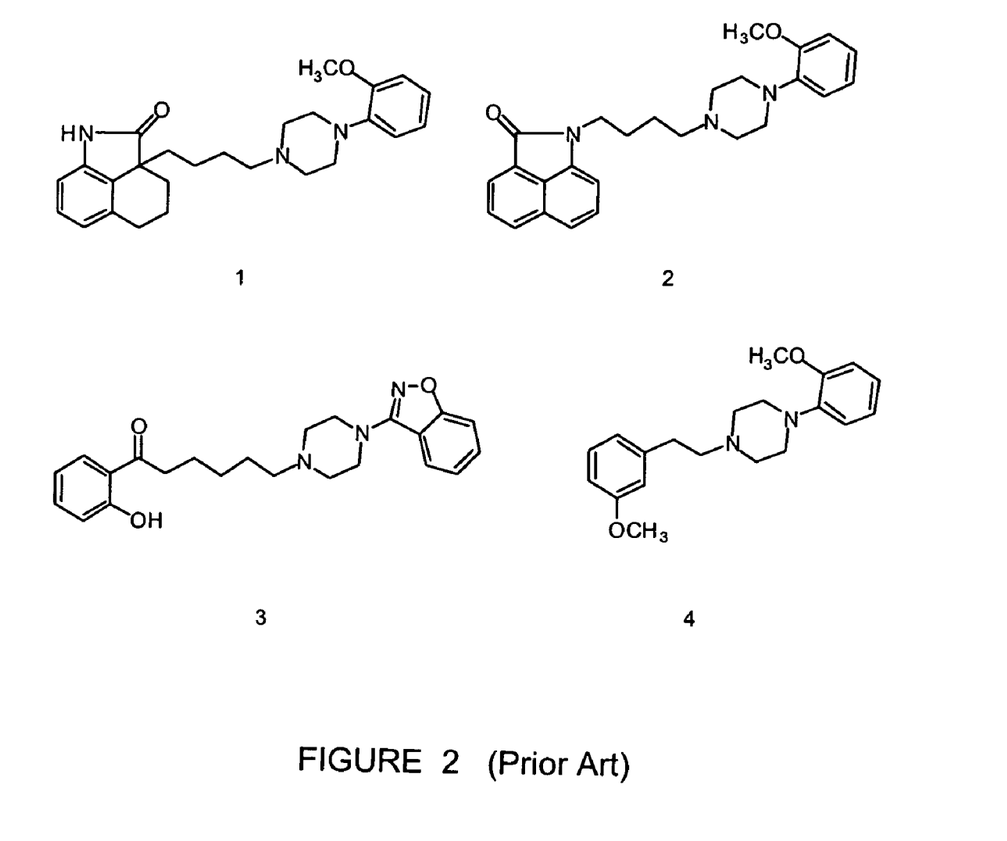
FIG. 2 provides the chemical structures of four species of prior art arylpiperazines.

Of the different chemical classes which bind to 5-HT$_7$Rs, arylpiperazines, four species of which are depicted and numbered in FIG. 2, have received our attention as well as that of other authors. Recently, we have reported structure affinity relationship studies of two distinct classes of 5-HT$_7$R ligands, based on the structure of 1-arylpiperazine. Examples of these classes are represented by compounds 3 and 4 (Perrone, R., Berardi, F., Colabufo, N. A., Lacivita, E., Leopoldo, M., Tortorella, V. *J. Med. Chem.* 2003, 46, 646-649; Leopoldo, M.; Berardi, F.; Colabufo, N. A.; Contino, M.; Lacivita, L.; Perrone, R.; Tortorella, V. *J. Pharm. Pharmacol.* 2004, 56, 247-255).

In the present study, we screened the 1-(2-methoxyphenyl) piperazine derivatives 5-7, previously prepared in our laboratory as 5-HT$_{1A}$ ligands (Perrone, et al. *J. Med. Chem.* 1996, 39, 3195-3202.

Perrone, R. et al. *J. Med. Chem.* 1998, 41, 4903-4909) against the cloned rat 5-HT$_7$R because they share some structural features with derivatives 1 and 2. We found that the compounds 6 and 7 possessed moderate affinities for 5-HT$_7$R, as well as for 5-HT$_{1A}$ receptor.

BRIEF DISCUSSION OF ASPECTS OF THE INVENTION

We here describe the structural modifications of compound 7, in particular modification in i) the intermediate alkyl chain length, ii) the presence and the position of the methoxy group on the 1,2,3,4-tetrahydronaphthalene nucleus, and iii) the position and the type of the aromatic substituent linked to the N-1 piperazine ring.

This experimental work has resulted in the identification of a novel family of high affinity 5-HT$_7$ receptor ligands based on the N-(1,2,3,4-tetrahydronaphthalen-1-yl)-4-(2 substituted-phenyl)-1-piperazinealkylamide structure.

One of several aspects of the present invention is therefore a family of 5-HT$_7$ receptor ligands having general formula I. A second aspect of the invention are compositions comprising the same ligands. A third aspect is the treatment of a human or animal subject in need thereof with one or more such compositions for any pathological state suitable of being relieved by these ligands or their pharmaceutically acceptable salts or other common derivatives.

The compounds of the invention are characterized by an extremely high affinity for the receptor 5-HT$_7$ and a considerable selectivity over 5-HT$_{1A}$ and 5-HT$_{2A}$ receptors.

Due to these affinity characteristics, various ligands of the invention find applicability in the treatment of those states suitable to be relieved by 5-HT$_7$ receptor agonists or antagonists.

DETAILED DESCRIPTION OF EMBODIMENTS OF THE INVENTION

Aspects of embodiments of the invention were published by the present inventors M. Leopoldo et al. in "Journal of Medicine Chemistry", Vol. 47, No. 26 pages 6616-6624, published on web on 19 Nov. 2004. This publication is specifically incorporated by reference by reference for any teaching not provided herein. Also, in reviewing the detailed disclosure which follows, it should be borne in mind that all patents, patent applications, patent publications, technical publications, scientific publications, and other references referenced herein are hereby incorporated by reference in this application in order to more fully describe the state of the art to which the present invention pertains.

It also is noted that compounds referred to by number correspond to the descriptions of the compounds as may be found in the accompanying tables and in the text.

Starting from N-(5-methoxy-1,2,3,4-tetrahydronaphthalen-1-yl)-4-(2-methoxyphenyl)-1-piperazinebutanamide (7), we have identified a new class of 5-HT$_7$R ligands. The structural modification introduced on 7 allowed the elucidation of the structural requirements for high 5-HT$_7$R affinity of this class of compounds. In particular, all structural modifications introduced on either the 1,2,3,4-tetrahydronaphthalenyl nucleus or on the linker between this particular group and the N-(2-methoxyphenyl)piperazine moiety influenced only the 5-HT$_7$R affinity and not the selectivity over 5-HT$_{1A}$ receptor. In contrast, modifications of the aryl group linked to the piperazine ring resulted in major changes in 5-HT$_7$R affinity. Therefore, the 4-aryl-N-(1,2,3,4-tetrahydronaphthalen-1-yl)-1-piperazinehexanamide structure was identified as a promising framework to obtain high affinity 5-HT$_7$R ligands. Among the compounds displaying the highest 5-HT$_7$R affinity, derivatives 28, 34, 44, 46, 49 were submitted to a functional assay to establish their intrinsic activity. Compounds 28, 44, and 49 behaved as full agonists, compound 34 as a partial agonist, whereas derivative 46 acted as an antagonist.

Among the compounds presented here, 4-(2-methylthiophenyl)-N-(1,2,3,4-tetrahydronaphthalen-1-yl)-1-piperazinehexanamide (44) was identified as a potent 5-HT$_7$R full agonist (K$_i$=0.22 nM, EC$_{50}$=2.56 μM), with selectivity over 5-HT$_{1A}$ and 5-HT$_{2A}$ receptors (200-fold and >1000-fold, respectively).

Preparation of the Compounds of the Invention

Figure 3:
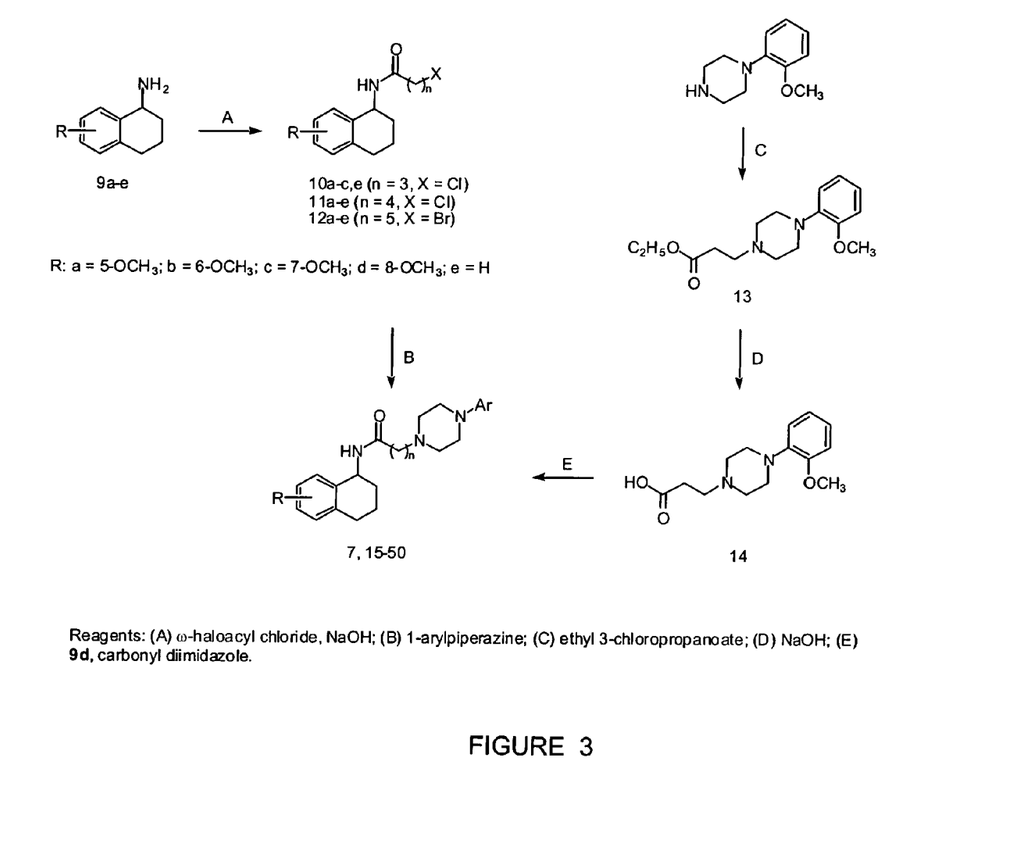
FIG. 3 provides a depiction of some of the synthetic pathways utilized in preparation of compounds of the invention.

Some of the synthetic pathways utilized in preparation of the compounds of the invention are depicted in Scheme 2, shown in FIG. 3. Acylation of amines 9a - e with the appropriate ω-haloacyl chloride afforded the key intermediates 10a-c,e, 11a-e, 12a-e that reacted with the appropriate 1-arylpiperazine to give the final compounds 7, 15-22, 24-50. This synthetic pathway was not useful to obtain derivative 23 in a pure form, therefore an alternative synthetic route was followed: 1-(2-methoxyphenyl)piperazine was reacted with ethyl 4-chorobutanoate to give ester 13. Hydrolysis of the latter gave carboxylic acid 14 that reacted with amine 9d to give the expected final compound. All target compounds were prepared as racemates.

The first modification performed on compound 7 was the optimization of the intermediate alkyl chain length. Therefore, we evaluated compounds 15 and 16 (Table 1) having a four or five methylene alkyl chain, respectively. 5-HT$_7$R affinity values indicated that alkyl chain elongation resulted in an increasing in affinity. Secondly, we shifted the methoxy group from the 5-position to the 6-, 7-, and 8-position of the tetrahydronaphthalenyl ring, because previous studies indicated that the position of the methoxy group on the terminal aromatic nucleus influenced the 5-HT$_7$R affinity of compounds 3 and 4 (Perrone R. et al. 2003 supra; Leopoldo M. et al 2004 supra) This modification was performed on the compounds 7, 15, and 16 that displayed good 5-HT$_7$R affinities. Considering each group of isomers (i.e. compounds having the same alkyl chain length), no significant difference in 5-HT$_7$R affinity was observed. Moreover, within each group of homologues (i.e. compounds bearing the methoxy group in the same position) affinity values replicate the affinity rank already noted for the 5-methoxy substituted derivatives 7, 15, and 16. Because the position of the methoxy group at the tetrahydronaphthalenyl ring did not exert a significant role on 5-HT$_7$R affinity of the compounds 7, 15-25, we evaluated the unsubstituted derivatives 26, 27, and 28. This modification improved the 5-HT$_7$R affinity.

The results in Table 1 indicate that the modifications of either the 1,2,3,4-tetrahydronaphthalenyl nucleus or of the linker between this group and the N-(2-methoxyphenyl)piperazine moiety of compound 7 influenced the 5-HT$_7$R affinity only and not the selectivity over 5-HT$_{1A}$ receptor.

Therefore, we focused on the aromatic ring attached to the piperazine nitrogen, bearing in mind that minimal changes in this part of the molecule might result in major changes in 5-HT$_7$R affinity as well as in 5-HT$_{1A}$ and 5-HT$_{2A}$ receptor affinity, as documented (Perrone R. et al. 2003 supra). Because the derivatives with a five methylene linker displayed the higher 5-HT$_7$R affinity values, we have further modified compound 28. Initially, based on literature data, we substituted the 2-methoxyphenyl group with a bicyclic aromatic system, or a 2-acetylphenyl, or a 2-cyanophenyl group. The replacement of the 2-methoxyphenyl group with a bicyclic aromatic system (Table 2, compounds 29-32) reduced the 5-HT$_7$R affinity. In particular, it can be noted that the presence of the benzisoxazolyl group was detrimental for 5-HT$_7$ affinity (compound 29), whereas in previous studies we found that this particular replacement resulted in the opposite effect (Perrone R. et al 2003 supra). In contrast, compounds 33 and 34 (Table 3) retained reasonably good 5-HT$_7$R affinity, but were unselective over 5-HT$_{1A}$ receptors. Moreover, we prepared compounds 35 and 36 that present an additional substituent in 4- or 3-position of the aromatic ring, because this substitution pattern has been reported to be detrimental for 5-HT$_{1A}$ receptor affinity. This modification determined a loss in 5-HT$_7$R affinity and no significant improvement in selectivity over 5-HT$_{1A}$ receptors. Additionally, we shifted the substituent from the 2-position of compounds 28, 33, and 34 to the 3- and 4 position (Table 3, derivative 37-42). Binding data of derivatives 37-42 indicate that affinity for 5-HT$_7$R strongly depends on the position of the substituent. In fact, the 3-substituted derivatives 37, 39, and 41 are less potent at 5-HT$_7$R than the 2-substituted isomers 28, 33, and 34. The 4-substituted derivatives 38, 40, and 42 are nearly devoid of 5-HT$_7$R affinity. Taken together, these data confirm that this part of the molecule is quite sensitive to minimal structural changes. Subsequently, we evaluated analogues of 28 having a substituent in the 2-position other than methoxy as well as the unsubstituted derivative (Table 3, derivatives 43-50). For this purpose we selected several substituents with different electronic properties. Considering the unsubstituted derivative 50 as reference compound, it can be noted that the cyano, chloro and nitro substituents (compounds 33, 47, and 48, respectively) did not change the 5-HT$_7$R affinity. In contrast, carboxamido and methylsulfonyl substituents (derivatives 43 and 45, respectively) caused a drop in 5-HT$_7$R affinity. Substitution of the 2-position by a methoxy, acetyl, methylthio, hydroxy, or methyl group resulted in high affinity 5-HT$_7$R ligands (derivatives 28, 34, 44, 46, 49, respectively). These data indicate that the presence of a substituent in the 2-position modulate the affinity of this class of compounds for 5-HT$_7$R. The affinity values seem not to be related to electronic, steric, or H-bonding properties of these substituents. As a result, clear structure-affinity relationships are not evident. Moreover, the 5-HT$_{1A}$ receptor affinities of compounds 33-50 parallel the 5-HT$_7$R affinities, whereas 5-HT$_{2A}$ receptor affinities are negligible. Notably, only compound 44 showed considerable selectivity over 5-HT$_{1A}$ and 5-HT$_{2A}$ receptors (200-fold and >1000-fold, respectively).

We tested the structurally related compounds 28, 34, 44, 46, and 49 for 5-HT$_7$ intrinsic activity in an isolated guinea-pig ileum assay (Table 4). It has been reported that 5-HT$_7$ agonists produce a dose-dependent guinea-pig ileum relaxation of substance P-induced contraction (Carter, D.; Champney, M.; Hwang, B.; Eglen, R. M. *Eur. J. Pharmacol.* 1995, 280, 243-250). Compounds 28, 44, and 49 behaved as full agonists, compound 34 as a partial agonist, whereas derivative 46 acted as an antagonist. These results indicate that the nature of the 2-substituent is related to the intrinsic activity. In particular, the difference in intrinsic activity between hydroxy derivative 46 and the corresponding methoxy derivative 28 might indicate that the H-bonding donor property of the hydroxy is responsible for the antagonistic property of 46. In contrast, an apolar group seems to promote the activation of 5-HT$_7$R.

Therapeutic Applications

Previous experimental reports demonstrated the potential role of 5-HT$_7$ receptors in circadian rhythms and sleep disorders (Lovenberg et al. supra).

There is also evidence supporting a possible role for 5-HT$_7$R in depression. Mullins et al. (supra) demonstrated that antidepressant-induced expression of the immediate early gene, c-Fos, in the SCN was blocked by ritanserin, a high-affinity, but non-selective, 5-HT$_7$R antagonist. This suggests that the effect is mediated through 5-HT$_7$Rs, although, with such non-selective antagonists, the involvement of other 5-HT receptors cannot be ruled out.

The involvement of the 5-HT$_7$R in migraine pathogenesis also has been proposed in literature Terron (supra) because the 5-HT$_7$R-mediated vasodilator mechanism operates in vascular structures that have been implicated in migraine, such as the middle cerebral and external carotid arteries. Finally, several compounds possessing high 5-HT$_7$R affinity have therapeutic indications as antipsychotic drugs and this has suggested that 5-HT$_7$R may mediate therapeutic action of such compounds.

The claimed compounds disclosed here are characterized by an extremely high affinity for the receptor 5-HT$_7$ with agonistic or antagonistic activity and a considerable selectivity over 5-HT$_{1A}$ and 5-HT$_{2A}$ receptors. These properties make the compounds of the invention effective therapeutic principles for the treatment of all those disorders in which the contribution of 5-HT$_7$ receptors is recognized, in particular in the treatment of circadian rhythms and sleep disorders and in the treatment of depression, psychotic states and migraine.

Pharmaceutical compositions comprising the ligands of the invention are compositions suitable for oral or parenteral administering. The active compounds may be formulated with any pharmaceutically acceptable eccipient in any suitable form such as tablets, capsules, pills, granulates, powder or aqueous, hydroalcolic, oleous solutions or W/O or O/W emulsions or dispersions.

Specific embodiments of the invention are solid compositions for oral use or liquid solutions for parenteral use comprising the compounds: 4-(2-methoxyphenyl)-N-(1,2,3,4-tetrahydronaphthalen-1-yl)-1-piperazinehexanamide (28), 4-(2-acetylphenyl)-N-(1,2,3,4-tetrahydronaphthalen-1-yl)-1-piperazinehexanamide (34), 4-(2-methylthiophenyl)-N-(1,2,3,4-tetrahydronaphthalen-1-yl)-1-piperazinehexanamide (44), 4-(2-hydroxyphenyl)-N-(1,2,3,4-tetrahydronaphthalen-1-yl)-1-piperazinehexanamide (46), 4-(2-methylphenyl)-N-(1,2,3,4-tetrahydronaphthalen-1-yl)-1-piperazinehexanamide (49). Among these, particular embodiments of the invention are compositions comprising the compound (44) that was identified as the most potent 5-HT$_7$ receptor agonist ($K_i$=0.22 nM, EC$_{50}$=2.56 µM), endowed with selectivity over 5-HT$_{1A}$ and 5-HT$_{2A}$ receptors (200-fold and >1000-fold, respectively).

EXAMPLES AND ADDITIONAL DISCLOSURE

Experimental Section

The following compounds were synthesized according to published procedures (See M. Leopoldo et al. "Journal of Medicine Chemistry" published on web on 19 Nov. 2004): 1-(2-acetylphenyl)piperazine, 1-(3-acetylphenyl)piperazine, 2-bromo(methylsulfonyl)benzene, 1-(2-carboxamidophenyl)piperazine, 1-(4-chloro-2-methoxyphenyl)piperazine, 1-(2-cyanophenyl)piperazine, 1-(3-cyanophenyl)piperazine, 1-(2,5-dimethoxyphenyl)piperazine, 5-methoxy-1,2,3,4-tetrahydro-1-naphthalenamine, 6-methoxy-1,2,3,4-tetrahydro-1-naphthalenamine, 7-methoxy-1,2,3,4-tetrahydro-1-naphthalenamine, 8-methoxy-1,2,3,4-tetrahydro-1-naphthalenamine, 1-(2-methylthiophenyl)piperazine, 1-(2-nitrophenyl)piperazine, 2-(1-piperazinyl)-1H-benzimidazole, 3-(1-piperazinyl)-1,2-benzisoxazole, 2-(1-piperazinyl)benzoxazole.

Column chromatography was performed with 1:30 ICN silica gel 60A (63-200 µm) as the stationary phase. Melting points were determined in open capillaries on a Gallenkamp electrothermal apparatus. Elemental analyses (C,H,N) were performed on Eurovector Euro EA 3000 analyzer; the analytical results were within ±0.4% of the theoretical values for the formula given. $^1$H NMR spectra were recorded at 300 MHz on a Bruker AM 300 WB spectrometer or on a Varian Mercury-VX spectrometer. All chemical shift values are reported in ppm (δ). Recording of mass spectra was done on an HP6890-5973 MSD gas chromatograph/mass spectrometer; only significant. m/z peaks, with their percentage of relative intensity in parentheses, are reported. Compounds 42, 43, and 45 were characterized by ESI$^+$/MS/MS with an Agilent 1100 Series LC-MSD trap System VL workstation. All spectra were in accordance with the assigned structures. The purity of new compounds that were essential to the conclusions drawn in the text were determined by HPLC on a Perkin-Elmer series 200 LC instrument using a Phenomenex Prodigy ODS-3 RP-18 column, (250°4.6 mm, 5 µm particle size) and equipped with a Perkin-Elmer 785A UV/VIS detector setting λ=254 nm. All compounds were eluted with $CH_3OH/H_2O/EtN_3$, 4:1:0.01, v/v, at a flow rate of 1 mL/min. A standard procedure was used to transform final compounds into their hydrochloride or oxalate salts that were recrystallized as detailed in Tables 1-3.

1-[2-(Methylsulfonyl)phenyl]piperazine (8)

A mixture of 2-bromo(methylsulfonyl)benzene (1.10 g, 4.7 mmol) and anhydrous piperazine (2.02 g, 23.5 mmol) was heated at 110° C. overnight. Then, the mixture was cooled and partitioned between 2 N NaOH and $CH_2Cl_2$. The separated organic layer was dried over $Na_2SO_4$ and concentrated under reduced pressure. The crude residue was chromatographed ($CHCl_3/CH_3OH$, 9:1, as eluent) to give 8 as a white semisolid (0.36 g, 34% yield). $^1$H NMR: δ 2.58 (s, 1H, NH, $D_2O$ exchanged), 2.84 (s, 4H, piperazinic), 3.14 (s, 3H, $CH_3$), 7.10-7.83 (m, 4H, aromatic).

General Procedure for Preparation of Alkylating Agents 10a-c,e, 11a-e, 12a-e

A cooled solution of amine 9 (4.0 mmol) in $CH_2Cl_2$ was stirred vigorously with 2% aqueous NaOH (9.6 mL, 4.8 mmol) while the appropriate ω-haloalkyl chloride (4.8 mmol) in $CH_2Cl_2$ was added dropwise. The same NaOH solution was then used to maintain pH at 9, and at constant pH the layers were separated. The organic phase was washed with 3 N HCl, with $H_2O$, and then dried over $Na_2SO_4$ and evaporated under reduced pressure. The crude residue was chromatographed as detailed below to give compounds 10a-c,e, 11a-e, 12a-e as white semisolids.

N-(5-Methoxy-1,2,3,4-tetrahydronaphthalen-1-yl)-4-chlorobutanamide (10a)

Eluted with $CHCl_3$/AcOEt, 1:1; 39% yield. $^1$H NMR: δ 1.72-1.86, 1.92-2.04 (m, 4H, endo $CH_2CH_2$), 2.10-2.19 (m, 2H, $CH_2CH_2CH_2$) 2.37 (t, 2H, J=7.2 Hz, $COCH_2$), 2.53-2.79 (m, 2H, benzylic $CH_2$), 3.63 (t, 2H, J=6.0 Hz, $CH_2Cl$), 3.82 (s, 3H, $CH_3$), 5.15-5.20 (m, 1H, CH), 5.75 (br d, 1H, NH), 6.72-7.18 (m, 3H, aromatic). GC-MS m/z 283 ($M^+$+2, 1), 281 ($M^+$, 2), 161 (26), 160 (100), 159 (27).

N-(5-Methoxy-1,2,3,4-tetrahydronaphthalen-1-yl)-5-chloropentanamide (11a)

Eluted with $CH_2Cl_2$; 33% yield. $^1$H NMR: δ 1.75-1.85, 1.93-2.01 (m, 8H, $CH_2(CH_2)_2CH_2$, endo $CH_2CH_2$), 2.19-2.26 (m, 2H, $COCH_2$), 2.55-2.73 (m, 2H, benzylic $CH_2$), 3.52-3.58 (m, 2H, $CH_2Cl$), 3.81 (s, 3H, $CH_3$), 5.14-5.19 (m, 1H, CH), 5.73 (br d, 1H, NH), 6.71-7.17 (m, 3H, aromatic). GC-MS m/z 297 ($M^+$+2, 2), 295 ($M^+$, 5), 161 (28) 160 (100), 159 (31), 145 (20).

N-(5-Methoxy-1,2,3,4-tetrahydronaphthalen-1-yl)-6-bromohexanamide (12a)

Eluted with $CH_2Cl_2$; 35% yield. $^1$H NMR: δ 1.43-1.53 [m, 2H, $(CH_2)_2CH_2(CH_2)_2$], 1.61-1.99 [m, 8H, $CH_2CH_2Br$, $COCH_2CH_2$, endo $CH_2CH_2$], 2.20 (t, 2H, J=7.4 Hz, $COCH_2$), 2.53-2.75 (m, 2H, benzylic $CH_2$), 3.40 (t, 2H, J=6.7 Hz, $CH_2Br$), 3.81 (s, 3H, $CH_3$), 5.17 (br t, 1H, CH), 5.69 (br d, 1H, NH), 6.74-7.17 (m, 3H, aromatic). GC-MS m/z 355 ($M^+$+2, 1), 353 ($M^+$, 1), 160 (100).

Ethyl 4-[4-(2-methoxyphenyl)piperazin-1-yl]butanoate (13)

A stirred mixture of 1-(2-methoxyphenyl)piperazine (1.50 g, 7.8 mmol), ethyl 4-bromobutanoate (0.9 mL, 6.3 mmol), and $K_2CO_3$ (0.87 g, 6.3 mmol) in acetonitrile was refluxed overnight. After the mixture was cooled, the mixture was evaporated to dryness and $H_2O$ (20 mL) was added to the residue. The aqueous phase was extracted with $CH_2Cl_2$ (2°30 mL). The collected organic layers were dried over $Na_2SO_4$ and evaporated under reduced pressure. The crude residue was chromatographed ($CHCl_3$/AcOEt, 1:1, as eluent) to afford pure 13 as a pale yellow oil (1.32 g, 68% yield). $^1$H NMR: δ 1.24 (t, 3H, J=7.1 Hz, $CH_2CH_3$), 1.79-1.89 (m, 2H, $CH_2CH_2CO$), 2.34 (t, 2H, J=7.3 Hz, $COCH_2$), 2.41 [t, 2H, J=7.4 Hz, $(CH_2)_2NCH_2$], 2.63 [br s, 4H, $(CH_2)_2NCH_2$], 3.06 [br s, 4H, $ArN(CH_2)_2$], 3.83 (s, 3H, $OCH_3$), 4.11 (q, 2H, J=7.1 Hz, $CH_2CH_3$), 6.82-7.00 (m, 3H, aromatic). GC-MS m/z 307 ($M^+$+1, 18), 306 ($M^+$, 77), 261 (32), 205 (100), 190 (37).

4-[4-(2-Methoxyphenyl)piperazin-1-yl)]butanoic acid (14)

Ester 13 (1.20 g, 3.9 mmol) was refluxed for 4 h in 20 mL of 4% aqueous NaOH. Then, the mixture was cooled and washed with $CHCl_3$. The separated aqueous phase was neutralized with 3 N HCl and extracted with AcOEt (3°30 mL). The collected organic layers were dried over $Na_2SO_4$ and evaporated under reduced pressure to give 0.58 g of acid 14 as a white solid (51% yield). $^1$H NMR: δ 1.84-1.89 (m, 2H, $CH_2CH_2CO$), 2.58-2.62 (m, 2H, $COCH_2$), 2.77 (br t, 2H, $(CH_2)_2NCH_2$], 2.2.96 [br s, 4H, $(CH_2)_2NCH_2$], 3.20 [br s, 4H, $ArN(CH_2)_2$], 3.87 (s, 3H, $CH_3$), 6.87-7.06 (m, 3H, aromatic), 9.52 (br s, 1H, OH, $D_2O$ exchanged). GC-MS m/z 279 ($M^+$+1, 20), 278 ($M^+$, 96), 219 (25), 205 (100), 190 (39).

General Procedure for Preparation of Final Compounds

A stirred mixture of alkylating agent 10a-c,e, 11a-e, 12a-e (8.0 mmol), 1-substituted piperazine (9.6 mmol) and $K_2CO_3$ (8.0 mmol) in acetonitrile was refluxed overnight. After cooling, the mixture was evaporated to dryness and $H_2O$ (20 mL) was added to the residue. The aqueous phase was extracted with AcOEt (2°30 mL). The collected organic layers were dried over $Na_2SO_4$ and evaporated under reduced pressure. The crude residue was chromatographed ($CH_2Cl_2/CH_3OH$, 19:1, as eluent) to yield pure compounds 7, 15-22, 24-43, 45-50. as pale yellow oils. Yields were between 20-30% for butanamide derivatives, 35-44% for pentanamide derivatives and 65-75% for the other compounds.

4-(2-Methoxyphenyl)-N-(1,2,3,4-tetrahydronaphthalen-1-yl)-1-piperazinebutanamide (26)

$^1$H NMR: δ 1.75-1.93, 1.98-2.10 (m, 6H, COCH$_2$CH$_2$, endo CH$_2$CH$_2$), 2.34 (t, 2H, J=7.0 Hz, COCH$_2$CH$_2$), 2.42-2.58 [m, 6H, CH$_2$N(CH$_2$)$_2$], 2.76-2.78 (m, 2H, benzylic CH$_2$), 2.90 [br s, 4H, (CH$_2$)$_2$NAr], 3.84 (s, 3H, CH$_3$), 5.19-5.29 (m, 1H, CH), 6.80-7.29 (m, 9H, aromatic, NH). GC-MS m/z 408 (M$^+$+1, 7), 407 (M$^+$, 27), 392 (88), 245 (52), 205 (100).

4-(2-Methoxyphenyl)-N-(1,2,3,4-tetrahydronaphthalen-1-yl)-1-piperazinepentanamide (27)

$^1$H NMR: δ 1.56-1.85, 2.01-2.07 [m, 8H, CH$_2$(CH$_2$)$_2$CH$_2$, endo CH$_2$CH$_2$], 2.25 (t, 2H, J=7.03 Hz, COCH$_2$CH$_2$), 2.43 [t, 2H, J=7.3 Hz, CH$_2$N(CH$_2$)$_2$], 2.62 [br s, 4H, CH$_2$N(CH$_2$)$_2$], 2.71-2.79 (m, 2H, benzylic CH$_2$), 3.06 [br s, 4H, (CH$_2$)$_2$NAr], 3.86 (s, 3H, CH$_3$), 5.19-5.23 (m, 1H, CH), 5.79 (br d, 1H, NH), 6.84-7.25 (m, 8H, aromatic). GC-MS m/z 422 (M$^+$+1, 4), 421 (M$^+$, 14), 406 (41), 259 (45), 205 (100), 131 (36).

4-(2-Methoxyphenyl)-N-(1,2,3,4-tetrahydronaphthalen-1-yl)-1-piperazinehexanamide (28)

$^1$H NMR: δ 1.36-1.43 (m, 2H, CH$_2$CH$_2$CH$_2$CH$_2$CH$_2$), 1.51-1.59, 1.61-1.86, 2.00-2.06 (m, 8H, CH$_2$CH$_2$CH$_2$CH$_2$CH$_2$, endo CH$_2$CH$_2$), 2.21 (t, 2H, J=7.6 Hz, COCH$_2$), 2.40 [br t, 2H, CH$_2$N(CH$_2$)$_2$], 2.64 [br s, 4H, CH$_2$N(CH$_2$)$_2$], 2.71-2.80 (m, 2H, benzylic CH$_2$), 3.09 [br s, 4H, (CH$_2$)$_2$NAr], 3.86 (s, 3H, CH$_3$), 5.17-5.23 (m, 1H, CH), 5.67 (br d, 1H, NH), 6.83-7.25 (m, 8H, aromatic). GC-MS m/z 436 (M$^+$+1, 4), 435 (M$^+$, 13), 420 (27), 273 (41), 205 (100).

4-(2-Acetylphenyl)-N-(1,2,3,4-tetrahydronaphthalen-1-yl)-1-piperazinehexanamide (34)

$^1$H NMR: δ 1.33-1.43 (m, 2H, CH$_2$CH$_2$CH$_2$CH$_2$CH$_2$), 1.51-1.86, 1.98-2.06 (m, 8H, CH$_2$CH$_2$CH$_2$CH$_2$CH$_2$, endo CH$_2$CH$_2$), 2.21 (t, 2H, J=7.4 Hz, COCH$_2$), 2.43 [t, 2H, J=7.6 Hz, CH$_2$N(CH$_2$)$_2$], 2.62 [br s, 4H, CH$_2$N(CH$_2$)$_2$], 2.65 (s, 3H, CH$_3$), 2.71-2.79 (m, 2H, benzylic CH$_2$), 3.04 [br t, 4H, (CH$_2$)$_2$NAr], 5.17-5.29 (m, 1H, CH), 5.69 (br d, 1H, NH), 7.02-7.40 (m, 7H, aromatic). GC-MS m/z 448 (M$^+$+1, 8), 447 (M$^+$, 26), 299 (60), 287 (65), 273 (100), 217 (90).

4-(2-Methylthiophenyl)-N-(1,2,3,4-tetrahydronaphthalen-1-yl)-1-piperazinehexanamide (44)

$^1$H NMR: δ 1.33-1.43 (m, 2H, CH$_2$CH$_2$CH$_2$CH$_2$CH$_2$), 1.53-1.63, 1.66-1.86, 2.00-2.06 (m, 8H, CH$_2$CH$_2$CH$_2$CH$_2$CH$_2$, endo CH$_2$CH$_2$), 2.22 (t, 2H, J=7.4 Hz, COCH$_2$), 2.40 (s, 3H, CH$_3$), 2.43 [t, 2H, J=7.4 Hz, CH$_2$N(CH$_2$)$_2$], 2.63 [br s, 4H, CH$_2$N(CH$_2$)$_2$], 2.74-2.79 (m, 2H, benzylic CH$_2$), 3.03 [br s, 4H, (CH$_2$)$_2$NAr], 5.18-5.29 (m, 1H, CH), 5.70 (br d, 1H, NH), 7.03-7.26 (m, 8H, aromatic). GC-MS m/z 452 (M$^+$+1, 2), 451 (M$^+$, 8), 273 (61), 221 (100).

4-(2-Methylphenyl)-N-(1,2,3,4-tetrahydronaphthalen-1-yl)-1-piperazinehexanamide (49)

$^1$H NMR: δ 1.34-1.44 (m, 2H, CH$_2$CH$_2$CH$_2$CH$_2$CH$_2$), 1.53-1.63, 1.66-1.86, 2.00-2.08 (m, 8H, CH$_2$CH$_2$CH$_2$CH$_2$CH$_2$, endo CH$_2$CH$_2$), 2.19 (t, 2H, J=7.4 Hz, COCH$_2$), 2.30 (s, 3H, CH$_3$), 2.42 [br t, 2H, CH$_2$N(CH$_2$)$_2$], 2.60 [br s, 4H, CH$_2$N(CH$_2$)$_2$], 2.70-2.79 (m, 2H, benzylic CH$_2$), 2.95 [br t, 4H, (CH$_2$)$_2$NAr], 5.18-5.23 (m, 1H, CH), 5.69 (br d, 1H, NH), 6.94-7.26 (m, 8H, aromatic). GC-MS m/z 420 (M$^+$+1, 2), 419 (M$^+$, 7), 273 (99), 189 (100).

N-(8-Methoxy-1,2,3,4-tetrahydronaphthalen-1-yl)4-(2-methoxyphenyl)-1-piperazinebutanamide (23)

A mixture of carboxylic acid 14 (0.50 g, 1.8 mmol) and 1,1'-carbonyldiimidazole (0.29 g, 1.8 mmol) in 10 mL of anhydrous THF was stirred for 8 h. A solution of amine 9d (0.32 g, 1.8 mmol) in 10 mL of anhydrous THF was added and the resulting mixture was stirred for 1 h. The reaction mixture was partitioned between AcOEt and H$_2$O. The organic layer was washed with aqueous Na$_2$CO$_3$ solution, dried (Na$_2$SO$_4$) and concentrated in vacuo. The crude residue was chromatographed (CH$_2$Cl$_2$/CH$_3$OH, 19:1, as eluent) to afford pure amide 23 (0.33 g, 42% yield). $^1$H NMR: δ 1.61-1.90, 2.10-2.19 (m, 6H, COCH$_2$CH$_2$, endo CH$_2$CH$_2$), 2.24 (t, 2H, J=7.4 Hz, COCH$_2$CH$_2$), 2.28-2.47, 2.55-2.58 [m, 6H, CH$_2$N(CH$_2$)$_2$], 2.68-2.77 (m, 2H, benzylic CH$_2$), 2.90 [br s, 4H, (CH$_2$)$_2$N], 3.79, 3.84 (2 s, 6H, 2 CH$_3$), 5.27-5.29 (m, 1H, CH), 6.46 (br d, 1H, NH), 6.67-7.18 (m, 7H, aromatic). GC-MS m/z 438 (M$^+$+1, 1), 437 (M$^+$, 4), 422 (27), 205 (24), 161 (100).

4-(2-Hydroxyphenyl)-N-(1,2,3,4-tetrahydronaphthalen-1-yl)-1-piperazinehexanamide (46)

A stirred mixture of alkyl bromide 12e (0.36 g, 1.1 mmol) and 1-(2-hydroxyphenyl)piperazine (0.29 g, 1.6 mmol) in acetonitrile was refluxed overnight. After the mixture was cooled, the solvent was evaporated in vacuo and a saturated aqueous solution of NaHCO$_3$ (20 mL) was added to the residue. The aqueous phase was extracted with AcOEt (2◦30 mL). The collected organic layers were dried over Na$_2$SO$_4$ and evaporated under reduced pressure. The crude residue was chromatographed (CHCl$_3$/CH$_3$OH, 19:1, as eluent) to yield pure 46 as a pale yellow oil (0.30 g, 65% yield). $^1$H NMR: δ 1.34-1.44 (m, 2H, CH$_2$CH$_2$CH$_2$CH$_2$CH$_2$), 1.53-1.63, 1.66-1.86, 2.00-2.07 (m, 8H, CH$_2$CH$_2$CH$_2$CH$_2$CH$_2$, endo CH$_2$CH$_2$), 2.22 (t, 2H, J=7.6 Hz, COCH$_2$), 2.43 [t, 2H, J=7.6 Hz, CH$_2$N(CH$_2$)$_2$], 2.63 [br s, 4H, CH$_2$N(CH$_2$)$_2$], 2.75-2.79 (m, 2H, benzylic CH$_2$), 2.90 [br s, 4H, (CH$_2$)$_2$NAr], 5.18-5.29 (m, 1H, CH), 5.69 (br d, 1H, NH), 6.83-7.27 (m, 9H, aromatic, OH, 1H D$_2$O exchanged). GC-MS m/z 422 (M$^+$+1, 2), 421 (M$^+$, 5), 273 (100), 191 (28).

Biological Methods.

General. Male Wistar Hannover rats (200-250 g) and male albino Dunkin-Hartley guinea-pigs (300-350 g) were from Harlan (S. Pietro al Natisone, Italy). The animals were handled according to internationally accepted principles for care of laboratory animals (E.E.C. Council Directive 86/609, O.J. No. L358, Dec. 18, 1986).

Rat recombinant serotonin 5-HT$_7$R expressed in HEK-293 cells were purchased from PerkinElmer-NEN (Betsville, Md., USA).

[$^3$H]-LSD, [$^3$H]-8-OH-DPAT, [$^3$H]-ketanserin were obtained from PerkinElmer-NEN (Zaventem, Belgium). 5-CT, substance P, and ketanserin were purchased from Tocris Cookson Ltd. (Bristol, UK). 8-OH-DPAT hydrobromide was from RBI. SB-269970 was purchased from Sigma-Aldrich (Milan, Italy).

For receptor binding studies, compounds 5-7, 15-50 were dissolved in absolute ethanol. For isolated guinea-pig ileum assay, compounds 28, 34, 44, 46, 49 were dissolved in Krebs-Henseleit solution, pH 7.4.

Radioligand Binding Assay at Rat Cloned 5-HT$_7$Rs. Binding of [$^3$H]-LSD at rat cloned 5-HT$_7$ receptor was performed according to a known method. In 1 mL of incubation buffer (50 mM Tris, 10 mM MgCl$_2$ and 0.5 mM EDTA, pH 7.4) were suspended 30 µg of membranes, 2.5 nM [$^3$H]-LSD, the drugs or reference compound (six to nine concentrations). The samples were incubated for 60 min at 37° C. The incubation was stopped by rapid filtration on GF/A glass fiber filters (pre-soaked in 0.5% polyethylenimine for 30 min). The filters were washed with 3◊3 mL of ice-cold buffer (50 mM Tris, pH 7.4). Nonspecific binding was determined in the presence of 10 µM 5-CT. Approximately 90% of specific binding was determined under these conditions.

Radioligand Binding Assay at Rat Hippocampal Membranes 5-HT$_{1A}$ Receptors. Binding experiments were performed according to a known method. Rats were killed by decapitation, the brain was quickly removed, and the hippocampus was dissected. The hippocampus (1.0 g) was homogenized with a Brinkman polytron (setting 5 for 3◊15 s) in 25 mL of 50 mM Tris buffer, pH 7.6. The homogenate was centrifuged at 48000 g for 15 min at 4° C. The supernatant was discarded, and the pellet was resuspended in 25 mL of buffer, then preincubated for 10 min at 37° C. The homogenate was centrifuged at 48000 g for 15 min at 4° C. The supernatant was discarded, and the final pellet was stored at −80° C. until used. Each tube received in a final volume of 1 mL of 50 mM Tris (pH 7.6) hippocampus membranes suspension and 1 nM [$^3$H]-8-OH-DPAT. For competitive inhibition experiments various concentrations of drugs studied were incubated. Nonspecific binding was defined using 1 µM 8-OH-DPAT. Samples were incubated at 37° C. for 20 min and then filtered on Whatman GF/B glass microfiber filters. The K$_d$ value determined for 8-OH-DPAT was 8.8 nM.

Radioligand Binding Assay at Rat Cortex Membranes 5-HT$_{2A}$ Receptors. Binding experiment was performed according to a known method. Rats were killed by decapitation, the brain was quickly removed, and the cortex was dissected. The cortex (1.0 g) was homogenized with a Brinkman polytron (setting 5 for 3◊15 s) in 25 mL of 0.25 M sucrose. The homogenate was centrifuged at 2000 g for 10 min at 4° C. The supernatant was saved, and the pellet was resuspended in 25 mL of buffer. The surnatantes were collected and diluted 1:10 w/w with 10 mM Tris pH 7.4. The homogenate was centrifugated at 35000 g for 15 min at 4° C. The supernatant was discarded, and the final pellet was stored at −80° C. until used. Each tube received, in a final volume of 2 mL of 50 mM Tris (pH 7.7), cortex membranes suspension and 2.5 nM [$^3$H]-ketanserin. For competitive inhibition experiments various concentrations of drugs studied were incubated. Nonspecific binding was defined using 10 µM ketanserin. Samples were incubated at 37° C. for 15 min and then filtered on Whatman GF/B glass microfiber filters. The K$_d$ value determined for ketanserin was 0.42 nM.

Isolated Guinea-Pig Ileum Assay. Guinea-pigs were anesthetized and then decapitated and the proximal ileum removed. The intestine was carefully flushed several times with warm Krebs-Henseleit solution (118 mM NaCl, 25 mM NaHCO$_3$, 4.7 mM KCl, 0.6 mM MgSO$_4$, 1.2 mM KH$_2$PO$_4$, 1.2 mM CaCl$_2$, 11.2 mM glucose, pH 7.4). Whole ileal segments, of about 3 cm in length, were suspended under 1.0 g tension in Krebs solution gassed with 95% O$_2$ and 5% CO$_2$ and maintained at 37° C. According to Eglen et al. (supra) with minor modification, the bathing medium contained 1 µM atropine to antagonize cholinergically mediated contractions due to activation of 5-HT$_3$ and 5-HT$_4$ receptors, 1 µM ketanserin to block 5-HT$_{2A}$ receptors, 1 µM pyrilamine to block H$_1$ receptors. Changes in tension of the tissue were recorded by Fort 10 Original WPI isometric transducer (2Biological Instruments, Italy) connected to a PowerLab/400 workstation. Tissue was contracted by 100 nM substance P. This value was preliminary determined by concentration-response curves (1 nM-200 nM). 100 nM substance P elicited 80% of maximum contraction. The reference agonist 5-CT or tested compound was added 3 min before substance P addition and non-cumulative concentration-response curves were constructed (0.001 µM-10 µM). Because we determined that 5-CT induced relaxation with maximal response (39%) at 3 µM concentration, 5-HT$_7$ desensitization was achieved by equilibrating for 1 h in the presence of 3 µM 5-CT changing the bathing solution every 15 min. Tested compounds were added 3 min before substance P addition.

Full agonists 5-CT, 28, 44, 49 and partial agonist 34 were also tested in the presence of the antagonist SB-269970 (0.1 µM-3 µM). The isolated guinea pig ileum was equilibrated for 75 min with antagonist before constructing concentration-response curves of tested compounds.

Tissue responses were recorded as gram changes in isometric tension and expressed as percentage of reduction in the height of the contraction.

Statistical Analysis. The inhibition curves on the different binding sites of the compounds reported in Table 1 were analyzed by nonlinear curve fitting utilizing the GRAPHPAD PRISM® program. The value for the inhibition constant, K$_i$, was calculated by using the Cheng-Prusoff equation. Agonist potencies, expressed as EC$_{50}$, were obtained from non-linear iterative curve fitting by GRAPHPAD PRISM®.

To the extent that compounds of the general formula I are optically active, the formula I includes both any isolated optical antipodes and the corresponding optionally racemic mixtures in any conceivable composition.

Various embodiments of the invention are foreseen to have valuable application as constituents of pharmaceutical preparations to treat various conditions generally defined as pathologies. Accordingly, embodiments of the invention also comprise pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin. Thus, based on the above, a variety of pharmaceutically acceptable doses are provided.

Also, it is noted that the term "pharmaceutically acceptable salt(s)" refers to salts derived from treating a compound of formula 1 with an organic or inorganic acid such as, for example, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, or similarly known acceptable acids.

Toward demonstration of various utilities of embodiments of the present invention, the following animal-based example is provided.

Example

Studies with hamsters show that systemic injections of 8-hydroxy-2-(di-n-propylamino)tetralin (8-OH-DPAT), a serotonergic agonist at the $5\text{-HT}_{1A/5A/7}$ receptors induce circadian phase advances. Microinjection of compound 44 into the dorsal raphe cause phase shift advances in a similar manner as did 8-OH-DPAT. Microinjection of the selective $5\text{-HT}_7$ receptor antagonist SB-26770-A into the dorsal raphe before microinjection of compound 44 significantly block phase shifts relative to pretreatment with vehicle (control). This provides evidence that no additional receptor subtype, such as the $5\text{-HT}_{1A}$ receptor or the $5\text{-HT}_{5A}$ receptor, is necessary for this effect.

Based on all of the above teachings and data, it is advanced that effective treatment of one or more states selected from a circadian rhythm disturbance, a sleep disorder, depression, psychosis, and migraine is achieved by administering a determined pharmaceutically acceptable dosage, comprising one or more of the above-disclosed $5\text{-HT}_7$ receptor agonists or antagonists, to a human or animal subject in need thereof. Such compounds are administered in a variety of forms that include, but are not limited to, pharmaceutical compositions as described above. Most simply, a dosage of one such compounds is administered to a human in need thereof, for a time regime determined based on the particular condition (i.e., pathology) and age, weight, etc. of the subject, and a desired effect with regard to the condition is obtained based on the selective action of the compound on $5\text{-HT}_7$ receptors.

Various embodiments of the present invention have been shown and described herein, and such embodiments provide teachings of various aspects of the invention. It is appreciated that variations, changes and substitutions may be made beyond these specific disclosures without departing from the invention herein. Accordingly, it is intended that the invention be limited only by the spirit and scope of the appended claims in accordance with the relevant law as to their interpretation.

TABLE 1

Physical Properties and Binding Affinities of Compounds 5-7, 15-28

| Compd | R | n | formula[a] | mp, °C. | $K_i$, nM 5-HT$_7$ | $K_i$, nM 5-HT$_{1A}$ |
|---|---|---|---|---|---|---|
| 5[b] | 5-CH$_3$O | 1 | — | — | >1000 | NT |
| 6[c] | 5-CH$_3$O | 2 | — | — | 269 ± 18 | 253 ± 25 |
| 7 | 5-CH$_3$O | 3 | C$_{26}$H$_{35}$N$_3$O$_3$•HCl•0.2H$_2$O | 215 dec | 35 ± 3.2 | 254 ± 65 |
| 15 | 5-CH$_3$O | 4 | C$_{27}$H$_{37}$N$_3$O$_3$•HCl•H$_2$O | 187-190 | 28.2 ± 4.20 | 54.4 ± 6.5 |
| 16 | 5-CH$_3$O | 5 | C$_{28}$H$_{39}$N$_3$O$_3$•2HCl•0.5H$_2$O | 194-197 | 20 ± 2.5 | 24.5 ± 1.8 |
| 17 | 6-CH$_3$O | 3 | C$_{26}$H$_{35}$N$_3$O$_3$•2HCl | 128-129 | 186 ± 40 | 257 ± 25 |
| 18 | 6-CH$_3$O | 4 | C$_{27}$H$_{37}$N$_3$O$_3$•2HCl | 149-152 | 43.1 ± 4.8 | 23.2 ± 2.3 |
| 19 | 6-CH$_3$O | 5 | C$_{28}$H$_{39}$N$_3$O$_3$•(COOH)$_2$ | 102-105 | 30 ± 3.15 | 55 ± 8.0 |
| 20 | 7-CH$_3$O | 3 | C$_{26}$H$_{35}$N$_3$O$_3$•2HCl•H$_2$O | 118-120 | 129 ± 5.0 | 160 ± 12 |
| 21 | 7-CH$_3$O | 4 | C$_{27}$H$_{37}$N$_3$O$_3$•2HCl•0.4H$_2$O | 187-188 | 38.4 ± 4.6 | 78.9 ± 6.30 |
| 22 | 7-CH$_3$O | 5 | C$_{28}$H$_{39}$N$_3$O$_3$•2HCl | 175-178 | 41 ± 11 | 39 ± 6.5 |

TABLE 1-continued

Physical Properties and Binding Affinities of Compounds 5-7, 15-28

| Compd | R | n | formula[a] | mp, °C | $K_i$, nM 5-HT$_7$ | 5-HT$_{1A}$ |
|---|---|---|---|---|---|---|
| 23 | 8-CH$_3$O | 3 | C$_{26}$H$_{35}$N$_3$O$_3$·2HCl | 131-133 | 154 ± 35 | 441 ± 20 |
| 24 | 8-CH$_3$O | 4 | C$_{27}$H$_{37}$N$_3$O$_3$·2HCl·0.2H$_2$O | 136-137 | 64.0 ± 12 | 72.0 ± 18 |
| 25 | 8-CH$_3$O | 5 | C$_{28}$H$_{39}$N$_3$O$_3$·2HCl | 125-127 | 31.4 ± 3.5 | 30.0 ± 2.6 |
| 26 | H | 3 | C$_{25}$H$_{33}$N$_3$O$_2$·2HCl | 171-173 | 92.0 ± 12 | 245 ± 20 |
| 27 | H | 4 | C$_{26}$H$_{35}$N$_3$O$_2$·2HCl·0.8H$_2$O | 199-200 | 6.05 ± 0.25 | 9 ± 0.70 |
| 28 | H | 5 | C$_{27}$H$_{37}$N$_3$O$_2$·2HCl·0.5H$_2$O | 150-151 | 6.64 ± 0.60 | 8.6 ± 0.35 |
| 5-CT | | | | | 0.51 ± 0.01 | |
| 8-OH-DPAT | | | | | | 1.2 ± 0.2 |

[a]All compounds were recrystallized from CH$_3$OH/Et$_2$O.
Analysis for C, H, N; results were within ±0.4% of the theoretical values for the formulas given.
[b]See ref. 33.
[c]See ref. 32.

TABLE 2

Physical Properties and Binding Affinities of Compounds 29-32

| compd | Ar | formula[a] | mp, °C | $K_i$, nM 5-HT$_7$ | 5-HT$_{1A}$ |
|---|---|---|---|---|---|
| 29 | (3-methyl-benzo[d]isoxazol-yl) | C$_{27}$H$_{34}$N$_4$O$_2$·2HCl·H$_2$O | 164 dec | 125 ± 30 | 3900 ± 120 |
| 30 | (2-methyl-benzoxazol-yl) | C$_{27}$H$_{34}$N$_4$O$_2$ | 148 dec | 820 ± 90 | NT[b] |
| 31 | (2-methyl-benzimidazol-yl) | C$_{27}$H$_{35}$N$_5$O·3HCl | 300 dec | 356 ± 55 | 2600 ± 280 |

TABLE 2-continued

Physical Properties and Binding Affinities of Compounds 29-32

| compd | Ar | formula[a] | mp, °C. | K$_i$, nM 5-HT$_7$ | K$_i$, nM 5-HT$_{1A}$ |
|---|---|---|---|---|---|
| 32 | 2-methyl-5-methoxybenzoxazole | C$_{28}$H$_{36}$N$_4$O$_3$•2HCl•H$_2$O | 196-198 | 704 ± 30 | NT |

[a] All compounds were recrystallized from CH$_3$OH/Et$_2$O except 30 (from CHCl$_3$/n-hexane).
Analysis for C, H, N; results were within ±0.4% of the theoretical values for the formulas given.
[b] Not tested.

TABLE 3

Physical Properties and Binding Affinities of Compounds 33-50

| cpd | R | formula[a] | mp, °C. | K$_i$, nM 5-HT$_7$ | K$_i$, nM 5-HT$_{1A}$ | K$_i$, nM 5-HT$_{2A}$ |
|---|---|---|---|---|---|---|
| 33 | 2-CN | C$_{27}$H$_{34}$N$_4$O•HCl•0.5H$_2$O | 175-178 | 48.7 ± 2.5 | 16.6 ± 1.4 | 700 ± 25 |
| 34 | 2-COCH$_3$ | C$_{28}$H$_{37}$N$_3$O$_2$•HCl•H$_2$O | 136-139 | 4.14 ± 0.80 | 3.8 ± 0.10 | 12200 ± 350 |
| 35 | 2-OCH$_3$-4-Cl | C$_{27}$H$_{36}$N$_3$O$_2$Cl | 145-147 | 122 ± 14 | 332 ± 27 | 7168 ± 150 |
| 36 | 2,5-di-OCH$_3$ | C$_{28}$H$_{39}$N$_3$O$_3$•2HCl•0.6H$_2$O | 124-126 | 70.3 ± 5.2 | 911 ± 23 | 259 ± 20 |
| 37 | 3-OCH$_3$ | C$_{27}$H$_{37}$N$_3$O$_2$•2HCl•0.5H$_2$O | 156-159 | 119 ± 20 | 105 ± 12 | 142 ± 20 |
| 38 | 4-OCH$_3$ | C$_{27}$H$_{37}$N$_3$O$_2$ | 129-130 | 2100 ± 150 | NT[b] | NT |
| 39 | 3-CN | C$_{27}$H$_{34}$N$_4$O•HCl | 170-172 | 97.8 ± 5.6 | 291 ± 15 | 909 ± 85 |
| 40 | 4-CN | C$_{27}$H$_{34}$N$_4$O•HCl•1.5H$_2$O | 102-104 | 1400 ± 120 | NT | NT |
| 41 | 3-COCH$_3$ | C$_{28}$H$_{37}$N$_3$O$_2$•2HCl•H$_2$O | 146-148 | 496 ± 24 | 676 ± 32 | 1127 ± 200 |
| 42 | 4-COCH$_3$ | C$_{28}$H$_{37}$N$_3$O$_2$•2HCl | 112-114 | 2639 ± 130 | NT | NT |
| 43 | 2-CONH$_2$ | C$_{27}$H$_{36}$N$_4$O$_2$•2HCl•0.5H$_2$O | 184-187 | 229 ± 12 | 494 ± 35 | >4000 (9%) |
| 44 | 2-SCH$_3$ | C$_{27}$H$_{37}$N$_3$OS•HCl•H$_2$O | 181-182 | 0.22 ± 0.08 | 52.7 ± 3.2 | 326 ± 35 |
| 45 | 2-SO$_2$CH$_3$ | C$_{27}$H$_{37}$N$_3$O$_3$S•HCl•H$_2$O | 120-122 | 298 ± 16 | 3124 ±260 | >4000 (38%) |
| 46 | 2-OH | C$_{26}$H$_{35}$N$_3$O$_2$•2HCl•0.3H$_2$O | 162-164 | 11.4 ± 2.3 | 24 ± 6.3 | 3394 ± 225 |
| 47 | 2-Cl | C$_{26}$H$_{34}$ClN$_3$O•HCl•0.3H$_2$O | 168-169 | 40.1 ± 6.7 | 96 ± 8.0 | 301 ± 12 |
| 48 | 2-NO$_2$ | C$_{26}$H$_{34}$N$_4$O$_3$•HCl•0.5H$_2$O | 152-155 | 63.3 ± 7.5 | 183 ± 15 | 282 ± 35 |
| 49 | 2-CH$_3$ | C$_{27}$H$_{37}$N$_3$O•2HCl•0.5H$_2$O | 212-214 | 15.2 ± 3.2 | 279 ± 44 | 262 ± 24 |
| 50 | H | C$_{26}$H$_{35}$N$_3$O•2HCl•0.5H$_2$O | 172-174 | 65.6 ± 4.7 | 128 ± 22 | 77.8 ± 5.7 |

[a] All compounds were recrystallized from CH$_3$OH/Et$_2$O except 35 and 38 (from CHCl$_3$/n-hexane).
Analysis for C, H, N; results were within ±0.4% of the theoretical values for the formulas given.
[b] Not tested.

TABLE 4

Relaxation effect induced by selected compounds and 5-CT on substance P-stimulated guinea pig ileum contracture with 5-HT$_7$ receptor desensitization.

| cpd | Maximal Effect % | EC$_{50}$, µM | PA$_2$ (vs SB-269970) | Schild plot | N |
|---|---|---|---|---|---|
| 28 | 91 | 6.32 ± 0.20 | 8.02 ± 1.40 | 1.0 (p < 0.0001) | 15 |
| 34 | 79 | 2.46 ± 0.70 | 7.60 ± 0.49 | 1.3 (p < 0.0001) | 14 |
| 44 | 100 | 2.56 ± 0.32 | 7.70 ± 0.80 | 0.9 (p < 0.0001) | 15 |
| 46 | 0 | — | 7.20 ± 0.60 | 1.6 (p < 0.005) | 16 |
| 49 | 98 | 1.82 ± 0.72 | 7.80 ± 0.40 | 0.9 (p < 0.0001) | 15 |
| 5-CT | 100 | 0.63 ± 0.04 | 7.48 ± 0.12 | 1.2 (p < 0.0001) | 12 |

We claim:

1. 5-hydroxytryptamine-7 (5-HT$_7$) receptor ligands, having general formula I

Formula I wherein:
R means 2-methoxy, 2-acetyl, 2-methylthio, 2-hydroxy, 2-methyl group and n means 4 or 5 or pharmaceutically acceptable salts thereof.

2. The 5-HT$_7$ receptor ligands of claim 1, wherein n is 5 and R is a methylthio group or n is 5 and R is a hydroxy group or n is 5 and R is a methyl group or n is 5 and R is a methoxy group or n is 4 and R is a methoxy group.

3. 5-HT$_7$ receptor ligands according to claim 1, wherein n is 5 and R is a methylthio group.

4. 5-HT$_7$ receptor ligands according to claim 1, wherein n is 5 and R is a hydroxy group.

5. 5-HT$_7$ receptor ligands according to claim 1, wherein n is 5 and R is a methyl group.

6. 5-HT$_7$ receptor ligands according to claim 1, wherein n is 5 and R is a methoxy group.

7. 5-HT$_7$ receptor ligands according to claim 1, wherein n is 4 and R is a methoxy group.

8. Pharmaceutic composition comprising a therapeutically effective amount of one or more 5-HT$_7$ receptor ligands according to claim 1 or a pharmaceutically acceptable salt thereof and a pharmaceutically acceptable excipient.

9. Pharmaceutic composition according to claim 8, comprising one or more ligands or pharmaceutically acceptable salts thereof selected from the group consisting of 4-(2-Methylthiophenyl)-N-(1,2,3,4-tetrahydronaphthalen-1-yl)-1-piperazinehexanamide (44); 4-(2-Methylphenyl)-N-(1,2,3,4-tetrahydronaphthalen-1-yl)-1-piperazinehexanamide (49); 4-(2-Methoxyphenyl)-N-(1,2,3,4-tetrahydronaphthalen-1-yl)-1-piperazinehexanamide (28); 4-(2-Methoxyphenyl)-N-(1,2,3,4-tetrahydronaphthalen-1-yl)-1-piperazinepentanamide (27); 4-(2-Acetylphenyl)-N-(1,2,3,4-tetrahydronaphthalen-1-yl)-1-piperazinehexanamide (34); 4-(2-Hydroxyphenyl)-N-(1,2,3,4-tetrahydronaphthalen-1-yl)-1-piperazinehexanamide (46) and a pharmaceutically acceptable excipient.

10. A method of treatment pathological states suitable to be relieved by 5-HT$_7$ receptor agonists or antagonists comprising the step of administering one or more 5-hydroxytryptamine-7 (5-HT$_7$) receptor ligands according to claim 1 to a subject in need, wherein the pathological state is selected from the group consisting of circadian rhythm disturbances and depression.

11. A method of preparing a compound according to claim 1 comprising acylating amines of formula 9e:

Formula 9e with the appropriate ω-haloacyl chloride of the following formula:

to obtain the corresponding intermediate compounds of formula 11e wherein X is chlorine or 12e wherein X is bromine:

Formula 11e, 12e reacting these intermediate compounds with the appropriate 1-(2-substituted phenyl) piperazine of the following formula:

and optionally reacting the obtained compound of formula I with a suitable acid to prepare its pharmaceutically acceptable salt, wherein R means 2-methoxy, 2-acetyl, 2-methylthio, 2-hydroxy, of 2-methyl group, and n means 4 or 5.

12. The method of claim 11, additionally comprising reacting the compound of Formula 1 with a suitable acid to prepare its pharmaceutically acceptable salt.

* * * * *